(12) United States Patent
Munro et al.

(10) Patent No.: US 10,603,401 B2
(45) Date of Patent: Mar. 31, 2020

(54) DRESSING SYSTEM

(71) Applicants: Edixomed Limited, Edinburgh Midlothian (GB); First Water Limited, Marlborough, Wiltshire (GB)

(72) Inventors: Hugh Munro, Edinburgh Midlothian (GB); Nicholas Boote, Marlborough (GB)

(73) Assignees: Edixomed Limited, Edinburgh Park (GB); First Water Limited, Marlborough (GB)

( * ) Notice: Subject to any disclaimer, the term of this patent is extended or adjusted under 35 U.S.C. 154(b) by 0 days.

(21) Appl. No.: 15/779,147

(22) PCT Filed: Nov. 28, 2016

(86) PCT No.: PCT/GB2016/053727
§ 371 (c)(1),
(2) Date: May 25, 2018

(87) PCT Pub. No.: WO2017/089831
PCT Pub. Date: Jun. 1, 2017

(65) Prior Publication Data
US 2018/0264164 A1 Sep. 20, 2018

(30) Foreign Application Priority Data
Nov. 27, 2015 (GB) .................................. 1520990.1

(51) Int. Cl.
| A61K 33/00 | (2006.01) |
| A61L 15/44 | (2006.01) |
| A61K 9/70 | (2006.01) |
| A61K 31/167 | (2006.01) |
| A61L 26/00 | (2006.01) |
| A61K 31/445 | (2006.01) |
| A61K 31/46 | (2006.01) |
| A61K 31/245 | (2006.01) |
| A61L 15/24 | (2006.01) |
| A61L 15/28 | (2006.01) |

(52) U.S. Cl.
CPC ............ *A61L 15/44* (2013.01); *A61K 9/7007* (2013.01); *A61K 31/167* (2013.01); *A61K 31/245* (2013.01); *A61K 31/445* (2013.01); *A61K 31/46* (2013.01); *A61K 33/00* (2013.01); *A61L 15/24* (2013.01); *A61L 15/28* (2013.01); *A61L 26/0066* (2013.01); *A61L 2300/114* (2013.01); *A61L 2300/402* (2013.01)

(58) Field of Classification Search
CPC .......... A61L 15/24; A61L 15/28; A61L 15/44; A61L 2300/402; A61L 2300/114; A61K 9/7007; A61K 33/00; A61K 31/167
USPC ......................................................... 424/445
See application file for complete search history.

(56) References Cited

U.S. PATENT DOCUMENTS

| 2010/0015208 A1 | 1/2010 | Kershaw et al. |
| 2015/0030702 A1 | 1/2015 | Jezek et al. |
| 2015/0086651 A1 | 3/2015 | Jezek et al. |

FOREIGN PATENT DOCUMENTS

| WO | 2006100154 A1 | 9/2006 |
| WO | 2008116497 A1 | 10/2008 |
| WO | 2014188174 A1 | 11/2014 |
| WO | 2014188175 A1 | 11/2014 |

OTHER PUBLICATIONS

Wiegand et al (title: Clinical efficacy of dressings for treatment of heavily exuding chronic wounds; Chronic Wound Care Management and Research, 2015, vol. 2; pp. 101-111, published Jun. 10, 2015) (Year: 2015).*
Boateng, et al., "Wound Healing Dressings and Drug Delivery Systems: A Review", Journal of Pharmaceutical Sciences, 2008, 97(8), pp. 2892-2923.
Gethin et al., "The impact of Manuka honey dressings on the surface pH of chronic wounds", Clinical Research, 2008, 5, pp. 185-194.

* cited by examiner

*Primary Examiner* — Yanzhi Zhang
(74) *Attorney, Agent, or Firm* — Stradley Ronon Stevens & Young, LLP

(57) ABSTRACT

The present invention relates to skin dressings that are useful in the treatment of conditions associated with tissue ischaemia and skin lesions including those that are infected, such as burns and surgical wounds and chronic wounds such as but not limited5 to diabetic foot ulcers and venous leg ulcers. The skin dressings are also useful to effect transdermal delivery of pharmaceutically active agents.

21 Claims, 7 Drawing Sheets

DRESSING SYSTEM

CROSS-REFERENCE TO RELATED APPLICATIONS

This application is a 35 U.S.C. § 371 national phase application of PCT Application No. PCT/GB2016/053727, filed Nov. 28, 2016, which claims priority to Great Britain Application No. 1520990.1, filed Nov. 27, 2015, each of which is incorporated herein by reference in its entirety.

FIELD OF THE INVENTION

The present invention relates to skin dressings that are useful in the treatment of conditions associated with tissue ischaemia and skin lesions including those that are infected, such as burns and surgical wounds and chronic wounds such as but not limited to diabetic foot ulcers and venous leg ulcers. The skin dressings are also useful to effect transdermal delivery of pharmaceutically active agents.

BACKGROUND OF THE INVENTION

Nitric oxide (NO) is a potent vasodilator, synthesised and released by vascular endothelial cells and plays an important role in regulating local vascular resistance and blood flow. Biologically, nitric oxide (NO) is generated from L-arginine via NO synthase enzymes and performs a variety of functions, including vasodilatation and host defence. NO is also manufactured on epithelial surfaces (such as in the mouth and stomach, and on the skin surface) in humans by sequential reduction of nitrate and nitrite. This relies on the synthesis of nitrite by the bacterial reduction of inorganic nitrate present in saliva, mucosal secretions or sweat. Nitrite is further reduced to NO in an acidic environment.

The combination of acid and nitrite is effective in killing a wide variety of pathogens by the generation of NO and oxides of nitrogen such as nitrogen dioxide ($NO_2$). It is likely that NO generated in this way has a significant role in host defence against microbial pathogens, many of which are known to be susceptible to this agent.

A system has previously been devised that mimics this endogenous mechanism of NO generation, using inorganic nitrite and an organic acid to produce NO on the skin surface. This method relies on keeping the components separate until applied directly to the skin. Individually, these components elicit no significant effects.

WO 2000/053193 relates to the use of acidified nitrite as an agent to cause local production of nitric oxide at the skin surface for the treatment of peripheral ischaemia and associated conditions such as Raynaud's phenomenon and wounds such as post-operative wounds and burns. In some embodiments, a barrier consisting of a membrane allows diffusion of the nitrite ions while preventing direct contact of the acidifying agent with the skin.

It has also previously been discovered that a system using inorganic nitrite and an organic acid to produce NO on the skin surface can be used for the transdermal delivery of pharmaceutically active agents.

WO 02/17881 discloses a transdermal delivery system comprising a pharmaceutically active agent and acidified nitrite as an agent to cause local production of nitric oxide at the skin surface. Also disclosed is the use of a barrier consisting of a membrane to allow diffusion of the pharmaceutically active agent and nitrite ions while preventing direct contact of the acidifying agent with the skin.

WO/2014/188174 and WO/2014/188175 describe systems comprising a layer containing a nitrite and a hydrogel that contains hydrogen ions. These disclosures originate from one or more of the members of the inventive entity of the present application.

SUMMARY OF THE INVENTION

The present inventors have developed an improved dressing system that is useful in the treatment of conditions associated with tissue ischaemia and skin lesions, including those that are infected, such as burns and surgical wounds and chronic wounds such as but not limited to diabetic foot ulcers and venous leg ulcers, and can also be used as a transdermal delivery system. The dressing makes use of a first layer containing a nitrite and a second layer containing a source of hydrogen ions to provide the acidifying effect on a nitrite for the production of NO. The inventors have surprisingly found that the heterogeneous reaction system created by these separate layers in such a dressing system is advantageous since it results in a reduced amount of the $NO_2$ by-product of the reaction to produce NO, whilst producing NO at therapeutic levels.

Accordingly, in a first embodiment the present invention provides a system comprising:
 (i) a layer containing a nitrite; and
 (ii) a layer comprising a source of hydrogen ions.

DETAILED DESCRIPTION OF THE INVENTION

The system of the invention is a dressing system. A "dressing", as will be well known to a person of skill in the art, is something that is applied to the skin of a human or animal to cover, protect and/or treat a lesion on the skin of the human or animal. A dressing is suitable for use in relation to any breakage or interruption in the skin barrier, which can be caused, for example, by ulcers, surgery, burns, cuts, lacerations, trauma and/or abrasions.

The system of the invention is a two component system, comprising a first component which comprises a layer containing a nitrite and a second component comprising a source of hydrogen ions. The layer comprising a source of hydrogen ($H^+$) ions has an acidic pH. The two components can in fact be considered as two separate dressings. When the two components are placed in contact with each other, a chemical reaction takes place to produce nitric oxide (NO). The two components will now be described in detail.

The first component of the system of the invention comprises or is a layer containing a nitrite. The layer is permeable (fully permeable or at least semi-permeable) to the diffusion of nitric oxide, which forms when the first and second components of the dressing are placed in contact with each other. The first component of the system of the invention is typically placed in direct contact with the skin (i.e. on a wound or ulcer) during use, and should not adhere to the skin and/or cause damage to the wound bed or friable wound tissue. The layer can therefore be described as a wound contact layer. The layer can therefore be made of any material that is suitable for this purpose and which can be impregnated with, imbibed with or otherwise contain a nitrite. The layer is typically, but not limited to, a mesh, non-woven bat, film, foam, alginate, amorphous hydrogel, crosslinked hydrogel or a membrane.

In one embodiment, the layer is a mesh. A mesh consists of connected strands of solid, typically flexible material, that form a lattice with holes or gaps through which certain substances can pass. The mesh can be woven or non-woven, but is typically non-woven.

The mesh is typically made of a polymeric material. Any polymeric material is suitable, for example viscose, polyamide, polyester, polypropylene or blends of these, but a preferred polymeric material is polypropylene.

In another embodiment, the layer is a dissolvable film. The term "dissolvable film" includes polymers with solubility in water. Examples include polyvinyl alcohols or polyvinylpyrrolidones and cellulose-based polymers for example hydroxypropylcellulose or carboxymethylcellulose.

Such a film can be made of any suitable material, for example cellulose.

In some embodiments, the system of the invention comprises a plurality of (i.e. more than one) layers containing a nitrite. For example, the system of the invention can comprise 2, 3, 4, 5, 6, 7, 8, 9 or 10 or more layers containing a nitrite. For example, the system of the invention can comprise a plurality of meshes imbibed with a nitrite, for example as a nitrite solution. Typically, when a plurality of layers is used, each of the layers is formed of the same material, for example a mesh or a dissolvable film.

In one embodiment, the layer is not a membrane and/or a gel, for example a hydrogel.

The layer contains a nitrite salt in solid or solution form. Typically, the nitrite is in the form of a nitrite solution. The layer is typically imbibed or impregnated with the nitrite, for example by soaking the layer in a solution of the nitrite. The nitrite is typically a pharmacologically acceptable source of nitrite ions or a nitrite precursor thereof.

The layer (such as a mesh) functions to retain the nitrite solution essentially within a region defined by the area of the layer (such as a mesh). This provides for ease of application of the dressing to the skin and/or wound.

The pharmacologically acceptable source of nitrite ions may be an alkaline metal nitrite or an alkaline earth metal nitrite. For example, $LiNO_2$, $NaNO_2$, $KNO_2$, $RbNO_2$, $CsNO_2$, $FrNO_2$, $Be(NO_2)_2$, $Mg(NO_2)_2$, $Ca(NO_2)_2$, $Sr(NO_2)_2$, $Ba(NO_2)_2$, or $Ra(NO_2)_2$. In a preferred embodiment the nitrite is sodium nitrite ($NaNO_2$), potassium nitrite ($KNO_2$) or calcium nitrite ($Ca(NO_2)_2$).

Alternatively, a nitrite precursor may be used as the source of the nitrite ions in the composition. Other sources of nitrite ions are nitrate ions derived from alkali metal or alkaline earth metal salts capable of enzymic conversion to nitrite. For example, $LiNO_3$, $NaNO_3$, $KNO_3$, $RbNO_3$, $CsNO_3$, $FrNO_3$, $Be(NO_3)_2$, $Mg(NO_3)_2$, $Ca(NO_3)_2$, $Sr(NO_3)_2$, $Ba(NO_3)_2$, or $Ra(NO_3)_2$.

The concentration of the nitrate/nitrite ion source in the layer containing a nitrite may be up to 20% w/w, suitably 0.25 to 15%, suitably 2 to 12%, suitably 4 to 10%, for example 5 to 8%. A particularly preferred concentration is 6% to 7% w/w.

Suitably, the final nitrite ion concentration present in the layer containing a nitrite is up to 20% w/w, generally in the range of from 0.25% to 15% w/w, for example 0.5% to 14% w/w, 1% to 13% w/w, suitably 2% to 12% w/w, suitably 3% to 11% w/w, suitably 4 to 10% w/w or 5 to 8% w/w. A particularly preferred nitrite ion concentration is 6% to 7% w/w.

If a solution of nitrite ions is being used, the molarity of the solution is typically from 0.01M to 2M, for example from 0.1M to 2M, for example from 0.2M to 1.8M, from 0.3M to 1.7M, from 0.4M to 1.6M, from 0.5M to 1.5M, for example around 0.7M, 0.8M, 0.9M, 1M, 1.1M, 1.2M or 1.3M.

In one specific embodiment, the first component of the dressing system is a polypropylene mesh or a plurality of polypropylene meshes impregnated with sodium nitrite, typically as a sodium nitrite solution.

In certain embodiments of the invention, which can optionally comprise a reductant, the amount (weight or volume) of nitrite solution can be used to control the amount of nitric oxide produced over time. Preferred amounts of sodium nitrite solution are from 5 mg to 100 mg per $cm^2$ of the area of nitrate containing layer (for example mesh) in contact with the layer comprising a source of hydrogen ions, for example from 10 mg to 85 mg per $cm^2$, from 20 mg to 75 mg per $cm^2$, from 30 mg to 60 mg per $cm^2$ or from 10 mg to 85 mg per $cm^2$. The second component of the dressing system of the invention provides a source of hydrogen ions. The second component is therefore acidic. Hydrogen ($H^+$) ions can alternatively be referred to as protons. By virtue of the presence of hydrogen ions, the second component reduces the pH at the site of application.

In certain embodiments the second component may be wetted prior or during use in order to enhance the availability of hydrogen ions.

When the second layer is placed in contact with the layer containing a nitrite, the acidic environment created by the second component allows the chemical reaction that produces nitric oxide from nitrite to take place. Thus, when the second layer is placed in contact with the layer containing a nitrite, nitric oxide is produced which diffuses through the layer containing a nitrite and onto or into the skin or wound bed of the patient. It can therefore be seen that the two components of the system of the invention are typically kept apart until use, to prevent nitric oxide from being generated prematurely. In accordance with the present invention, a minimal amount of nitrogen dioxide is produced as a by-product of the reaction.

Without wishing to be bound by theory, when the layer comprising a source of hydrogen ions is placed on top of the first component of the system (the layer or layers containing a nitrite), hydrogen ions are released and diffuse down a concentration gradient through the layer comprising a source of hydrogen ions and into the layer containing a nitrite, where they react with the nitrite to produce nitric oxide. A second process occurs where the nitrite solution or layer containing the nitrite is absorbed by the layer containing a source of hydrogen ions and the reaction takes place at the surface of or within the interface between the layers; the nitric oxide is released through the layer containing the nitrite into the tissue. The two components of the system therefore form a heterogeneous reaction system where they come into contact with one another. The meaning of a heterogeneous reaction system will be clear to the skilled reader, but it is important to note that it is distinct from a homogenous system (i.e., a system where all components and reactants are mixed). Without wishing to be bound by theory, the inventors believe the heterogeneous reaction system formed at the interface of the two layers contributes to the surprisingly low amount of $NO_2$ generated by the system of the invention. Furthermore, the use of heterogeneous reaction system generates a surprising amount of HONO, which further contributes to the production of NO from nitrite. These surprising and unexpected properties resulting from the use of a heterogeneous reaction system allow for the use of materials in the layer containing a source of hydrogen ions which would previously have been considered unsuitable, while maintaining (or even enhancing) the level of therapeutic NO produced and minimizing the production of undesirable $NO_2$. Until now it was assumed that acidification of nitrite would give rise to equimolar ratios of NO and $NO_2$.

Suitable materials that may act as the layer comprising a source of hydrogen ions include, but are not limited to Gelling fibres e.g. carboxymethyl cellulose, (e.g. Aquacel), alginates and mixtures thereof, superabsorbent dressings based on sodium polyacrylate e.g. Sorbion, honey dressings such as manukka honey based dressings, e.g. based on Active Leptospermum Honey e.g. Medihoney HCS. In preferred embodiments, the layer comprising a source of hydrogen ions is not a hydrogel. In other preferred embodiments, the layer comprising a source of hydrogen ions is not a hydrogel comprising a copolymerised acidic function into the polymer network of the hydrogel.

In certain embodiments the layer comprising a source of hydrogen ions may be wetted prior to use, i.e., it may be combined with water.

When wetted with an aqueous solution, the pH of the layer comprising a source of hydrogen ions is typically from pH2 to pH6, for example from pH2.5 to pH5.9, from pH2.6 to pH5.8, from pH2.7 to pH5.7, from pH2.8 to pH5.6, from pH2.9 to pH5.5, from pH3 to pH5.4, from pH3.1 to pH5.3, from pH3.2 to pH5.2, from pH3.3 to pH5.1, from pH3.4 to pH5, from pH3.5 to pH4.9, from pH3.6 to pH4.8, from pH3.7 to pH4.7, from pH3.8 to pH4.6, from pH3.9 to pH4.5, for example around pH4, pH4.1, pH4.2, pH4.3 or pH4.4. Preferably, the pH of the layer comprising a source of hydrogen ions is below around 5.5.

The present invention is derived from have previously devised a dressing system in which it is preferable for the $pK_a$ of the monomer or one of the monomers in a hydrogel to be within 1 unit of the pH of the hydrogel. Such a dressing system is described in International Application No. PCT/GB2014/051543 (published as WO/2014/188174) and International Application No. PCT/GB2014/051544 (published as WO/2014/188175), which are incorporated herein by reference in their entirety.

The layer comprising a source of hydrogen ions may contain a pH buffer to maintain the pH in the range 2-4.5. However, the addition of a pH buffer is typically not required.

The thickness of the layer comprising a source of hydrogen ions is typically up to 4 mm, typically 0.5-2 mm, more typically 1-2 mm, even more typically 1-1.6 mm.

In one embodiment, the layer comprising a source of hydrogen ions also contains a solid layer within it to provide mechanical strength, for example for processing purposes. The solid layer can be made of any suitable material and in one embodiment is a mesh, suitably made of a polymer, suitably a polypropylene mesh. The solid layer is suitably provided in the middle of the layer, for example in the form of a "sandwich" wherein the solid layer is sandwiched in between two layers of material.

In one embodiment, the layer comprising a source of hydrogen ions also has a barrier layer, for example a film such as a polyurethane film or an adhesive coated polyurethane film, on one of its external surfaces, typically on the surface that will be exposed to the air when in use. This layer typically provides a bacterial barrier. In certain other embodiments, the system may comprise a third layer, wherein the third layer comprises a barrier layer, for example a film such as a polyurethane film or an adhesive coated polyurethane film, on one of its external surfaces, typically on the surface that will be exposed to the air when in use. This third layer comprising a barrier layer would then a bacterial barrier. Preferably, the third layer is placed on top of the other layers of the system.

In one embodiment, the system of the first aspect of the invention further contains a pharmaceutically active agent. In this embodiment, the NO produced by the system is used to deliver the pharmaceutically active agent transdermally. The pharmaceutically active agent may be present either in the layer containing a nitrite or in the layer comprising a source of hydrogen ions.

If the pharmaceutically active agent is present in the layer containing the nitrite, the layer is typically imbibed or impregnated with the pharmaceutically active agent, for example by soaking the layer in a solution of the pharmaceutically active agent. This can be done at the same time as imbibing or impregnating the layer with the nitrite. For example, the layer can be soaked in a solution comprising a mixture of a nitrite and the pharmaceutically active agent for this purpose.

If the pharmaceutically active agent is present in the layer comprising a source of hydrogen ions, the pharmaceutically active agent is typically incorporated into the layer, or is present on the surface of the layer, in any suitable format.

When it contains a pharmaceutically active agent, the system of the invention can be used for the transdermal delivery of any pharmaceutically active agent.

The pharmaceutically active agent may comprise any suitable drug or combination of drugs to treat a disease in a patient. The agent may be immediately active in the form administered or may become active in the body of the patient following administration, such as for example through hydrolysis or by the action of an endogenous enzyme.

Therapeutically, the system of the invention can facilitate the delivery of a wide number of systemically active substances. Active substances include, but are not limited to, antibiotics, hormones, proteins, peptides, proteoglycans, nucleotides, oligonucleotides (such as DNA, RNA, etc.), vitamins, minerals, growth factors, non-steroidal anti-inflammatory drugs (NSAIDs) and vaccines. In certain embodiments the active substance may be an antimicrobial agent. Antimicrobial agents include, but are not limited to, Silver, Octenidine, Chlorhexidine gluconate, and Iodine. In a preferred embodiment, the delivery system of the present invention can be used to deliver anaesthetic, analgesic, hormone, immunosuppressant or steroid formulations. Other pharmaceutical agents include, but are not limited to, analgesic agents such as ibuprofen, indomethacin, diclofenac, acetylsalicylic acid, paracetamol, propranolol, metoprolol, oxycodone, thyroid releasing hormone, sex hormones such as oestrogen, progesterone and testosterone, insulin, verapamil, vasopressin, hydrocortisone, scopolamine, nitroglycerine, isosorbide dinitrate, anti-histamines (such as terfenadine), clonidine and nicotine, non-steroidal immunosuppressant drugs (such as cyclosporin, methotrexate, azathioprine, mycophenylate, cyclophosphamide, TNF antagonists), anticonvulsants and other drugs for dementia/Alzheimer's/Parkinson's disease such as apamorphone and rivastigmine, and steroids.

Typically, the pharmaceutically active agent is an anaesthetic. The anaesthetic can be any appropriate anaesthetic for local anaesthesia and can be provided in aqueous or powdered form, for example, lignocaine (lidocaine), amethocaine (tetracaine), xylocaine, bupivacaine, prilocaine, ropivacaine, benzocaine, mepivocaine or cocaine, or a mixture thereof, preferably in the hydrochloride form.

The general concentration range is around 1 to 4%, up to 10% w/w, although greater or lesser amounts can be empirically determined by a physician. Suitably preferred concentrations are tetracaine (0.01 to 10% w/w, suitably 1 to 8% w/w, preferably 2% w/w), lidocaine (0.01 to 10% w/w, suitably 1 to 8% w/w, preferably 5% or 10% w/w) and cocaine (1 to 4% w/w). Generally accepted safe dosages of such compounds for topical anaesthesia in a healthy 70 kg-adult are 750 mg for lidocaine, 200 mg for cocaine, and 50 mg for tetracaine. Other suitable anaesthetics are within the competence of the medical practitioner and can also be used in the system of the present invention at the relevant concentrations.

Prior art methods of improving local anaesthesia have suggested the use of low concentrations of vasoconstrictors, such as phenylephrine (0.005%). However, the compositions of the present invention utilise a previously unknown property of an acidified nitrite composition to produce NO, a vasodilator, which accelerates the transfer of anaesthetic into the dermis. The combination of the NO-generating system and anaesthetic will promote patient compliance of venepuncture and bloodletting techniques by reducing the pain experienced during the procedure and reducing associated infection.

The choice of pharmaceutically active agent may be determined by its suitability for the treatment regimen of the disease or medical condition concerned and reference can be made to standard reference works such as Martindale, the Merck Index, Goodman & Gilman's "The Pharmacological Basis of Therapeutics", 10th edition (2001), McGraw Hill and the British National Formulary (http://www.bnf.org/bnf/index.htm).

It should be emphasised that when it contains a pharmaceutically active agent the system of the invention is typically used to deliver a pharmaceutically active agent other than nitric oxide, i.e. the pharmaceutically active agent is not nitric oxide.

In use, the second component of the dressing system (containing a source of hydrogen ions) is placed on top of the first component of the dressing system (the layer containing a nitrite). The second component has a number of functions. Firstly, by virtue of the presence of hydrogen ions that are released from this component, the second component creates an acid environment for the conversion of nitrite to nitric oxide. Also, the second component of the dressing system is typically larger than the first component, and is of a suitable size and shape that when it overlays the first component it entirely covers the first component, such that there is an area on one or more of its edges, and typically all the way round the first component, that is in contact with the skin of the patient (although the second component is typically not in contact with a wound; rather, the first component of the dressing system is typically in contact with a wound when the dressing system is a wound dressing system). The second component may be adhesive and so, in this configuration, the second component retains the first component in place on the skin of a patient, typically over an ulcer or wound, in a manner analogous to that of a plaster (or BandAid™).

Since the system of the invention is a dressing useful, for example, for the treatment of ulcers and wounds, it is adapted for transdermal administration. The components of the system of the invention may be prepared by any method known in the art of pharmacy, and are typically prepared under sterile conditions.

The system of the invention is a two component system, comprising a first component which comprises a layer or a plurality of layers containing a nitrite and a second component comprising a source of hydrogen ions. In one embodiment, the system of the invention does not contain any other components. In this embodiment, the system consists of or consists essentially of a first component which comprises a layer or a plurality of layers containing a nitrite and a second component comprising a source of hydrogen ions. In one embodiment, the first component consists of or consists essentially of a (typically permeable) layer or plurality of layers containing a nitrite. In another embodiment, the second component consists of or consists essentially of a source of hydrogen ions.

The system of the invention typically does not contain certain other substances. In particular, the system itself or one or both of its components typically does not contain a thiol and/or a reductant, typically a non-thiol reductant, or only contains these substances in trace amounts, i.e. less than 0.05%, typically less than 0.01%, more typically less than 0.005% by weight of the system, or one or both components thereof. Thiols include glutathione (typically L-glutathione), 1-thioglycerol, 1-thioglucose, cysteine, and methyl- or ethyl-ester of cysteine, N-acetylcysteine, mercaptoethylamine and 3-mercaptopropanoic acid. Non-thiol reductants include iodide anion, butylated hydroquinone, tocopherol, butylated hydroxyanisole, butylated hydroxytoluene and beta-carotene, erythrobate or α-tocopherol, ascorbic acid (vitamin C). In some embodiments, the system itself or one or both of its components does not contain a source of $Cu^{2+}$ $Zn^{2+}$ and/or $Fe^{2+}$ ions.

In one embodiment, the first component does not contain a thiol and/or a reductant, typically a non-thiol reductant. In another embodiment, the second component does not contain a thiol and/or a reductant, typically a non-thiol reductant. In another embodiment, both the first component and the second component do not contain a thiol and/or a reductant, typically a non-thiol reductant.

In one embodiment, the first component does not contain a source of $Cu^{2+}$ $Zn^{2+}$ and/or $Fe^{2+}$ ions. In another embodiment, the second component does not contain a source of $Cu^{2+}$ $Zn^{2+}$ and/or $Fe^{2+}$ ions. In another embodiment, both the first component and the second component do not contain a source of $Cu^{2+}$ $Zn^{2+}$ and/or $Fe^{2+}$ ions.

The dressing system of the invention has either (a) two active components: the layer comprising a source of hydrogen ions and the layer containing a nitrite; or (b) three active components: the layer comprising a source of hydrogen ions, the layer containing a nitrite and a pharmaceutically active agent. No other active components are necessary for the functioning of the dressing system of the present invention.

The present inventors have now surprisingly found that the use of a heterogeneous reaction system is advantageous as it limits the amount of $NO_2$ by-product in the reaction that occurs to produce NO. This is demonstrated in the Examples of the present application.

In a second aspect, the present invention provides the system of the first aspect of the invention for use in medicine.

In a third aspect, the present invention provides the system of the first aspect of the invention for use in the treatment of a condition associated with tissue ischaemia or a wound. This aspect of the invention also extends to the use of a layer containing a nitrite and a layer comprising a source of hydrogen ions in the manufacture of a medicament for the treatment of a condition associated with tissue ischaemia or a wound.

This aspect of the invention also extends to:

A layer containing a nitrite for use in the treatment of a condition associated with tissue ischaemia or a wound, wherein said layer is administered simultaneously, separately or sequentially with a layer comprising a source of hydrogen ions.

A layer comprising a source of hydrogen ions for use in the treatment of a condition associated with tissue ischaemia or a wound, wherein said layer is administered simultaneously, separately or sequentially with a layer containing a nitrite.

Use of a layer containing a nitrite in the manufacture of a medicament for the treatment of a condition associated with tissue ischaemia or a wound, wherein said layer is administered simultaneously, separately or sequentially with a layer comprising a source of hydrogen ions.

Use of a layer comprising a source of hydrogen ions in the manufacture of a medicament for the treatment of a condition associated with tissue ischaemia or a wound, wherein said layer is administered simultaneously, separately or sequentially with a layer containing a nitrite.

A system comprising a layer containing a nitrite and a layer comprising a source of hydrogen ions as a combined preparation for simultaneous, separate or sequential use in treating a condition associated with tissue ischaemia or a wound.

This aspect of the invention also extends to a method of treatment of a condition associated with tissue ischaemia or a wound comprising administering a system of the first aspect of the invention to a subject in need thereof. The subject is a patient having a condition associated with tissue ischaemia or a wound, as described herein. The method typically comprises administering to the patient the first component described herein and then subsequently administering the second component described herein, on top of the first component. Tissue ischaemia is a restriction of the blood supply to tissues. In some embodiments, the tissue ischaemia is peripheral ischaemia, i.e. where peripheral circulation is restricted, for example skin ischaemia.

In some circumstances, damage to the skin leads to tissue ischaemia as the blood supply is reduced or prevented by the body's own repair or defence mechanisms.

Conditions associated with tissue ischaemia include Raynaud's syndrome, severe primary vasospasm and tissue ischaemia caused by septic shock or irradiation or a peripheral vascular disease (for example caused by diabetes and other chronic/systemic diseases), as well as post-surgical tissue ischaemia.

The present invention is also useful in the treatment of wounds. Wounds include ulcers, skin donor sites, surgical wounds (post-operative), burns (for example scalds, superficial, partial thickness and full thickness burns), lacerations and abrasions, and can be chronic or acute. Some burns (for example full thickness and some partial thickness burns) are also associated with tissue ischaemia. Ulcers can be of various origin, for example of venous or arterial origin, and include leg ulcers, pressure ulcers, venous ulcers and ulcers associated with diabetes such as diabetic foot ulcers. The present invention is also useful in the treatment of wounds that are infected.

Dosages of nitric oxide, which is the active substance produced by the system of the present invention when it does not contain an additional pharmaceutically active agent, can vary between wide limits, and can be tailored depending upon the disease or disorder to be treated, the severity of the condition, and the age and health of the individual to be treated, etc. A physician will ultimately determine appropriate dosages to be used. The system is configured so as to deliver nitric oxide in a therapeutically active amount, which is an amount that ameliorates or eliminates the symptoms of the condition (such as an ulcer or wound) that is being treated. As described herein, the system of the present invention can be used to control the amount and duration of nitric oxide release.

This dosage may be repeated as often as appropriate. If side effects develop the amount and/or frequency of the dosage can be reduced or otherwise altered or modified, in accordance with normal clinical practice.

The system of the invention may be formulated for use in human or for veterinary medicine. The present application should be interpreted as applying equally to humans as well as to animals, unless the context clearly implies otherwise.

In a fourth aspect, the present invention provides a kit comprising a layer containing a nitrite and a layer comprising a source of hydrogen ions as a combined preparation for simultaneous, separate or sequential use in treating a condition associated with tissue ischaemia or a wound. The kit is suitably provided with instructions for use in the treatment of a condition associated with tissue ischaemia or a wound.

When the system of the first aspect of the invention also comprises a pharmaceutically active agent, the invention also extends to the use of such a system for the treatment of a disease or condition other than a condition associated with tissue ischaemia or a wound.

Accordingly, in a fifth aspect, the present invention provides the system of the first aspect of the invention comprising a pharmaceutically active agent for use in the treatment of a disease or medical condition. Medical conditions that can be treated using the system of the present invention comprising a pharmaceutically active agent include pain, wherein the system of the invention is used to provide local anaesthesia, and transplant rejection, wherein the system of the invention is used to provide the effect of immunosuppression. Pain includes chronic and acute pain, post-operative pain and neuropathic pain. Diseases suitable for treatment using the system of the present invention comprising a pharmaceutically active agent include but are not limited to cardio-vascular diseases, neurological diseases or disease of the central nervous system, (e.g. multiple sclerosis, Parkinson's Disease), epilepsy, psychiatric disorders (e.g. schizophrenia), inflammation (e.g. rheumatoid arthritis, osteoarthritis, asthma, gout), in particular topical inflammation, hypertension, arrhythmia, hyperlipoproteinemias, gastrointestinal disorders (e.g. peptic ulcers), kidney disease, parasite infections (e.g. protozoal infection, helminthiasis, amebiasis, giardiasis, thichomoniasis, leishmaniasis, trypanosomiasis, malaria), microbial infection (e.g. yeast, fungus, bacteria), viral infection, cancer, immunosuppression, blood disorders (blood clots etc.), endocrine (e.g. hormonal) disorders (e.g. thyroid condition, hypoglycaemia), diabetes, dermatological disorders (e.g. psoriasis). It will be understood that the disease to be treated using the system of the invention will depend on the nature of the pharmaceutically active agent that to be delivered transdermally using the system of the present invention.

In one embodiment, the present invention provides the system of the first aspect of the invention for use in the treatment of pain, wherein the pharmaceutically active agent is an anaesthetic selected from the group consisting of lignocaine (lidocaine), amethocaine (tetracaine), xylocaine, bupivacaine, prilocaine, ropivacaine, benzocaine, mepivocaine, cocaine or a mixture thereof. In this embodiment, the treatment of pain is typically local anaesthesia.

This aspect of the invention also extends to the use of a layer containing a nitrite and a layer comprising a source of hydrogen ions in the manufacture of a medicament for the treatment of a disease or medical condition, wherein the layer containing a nitrite and/or the layer comprising a source of hydrogen ions comprises a pharmaceutically active agent. In particular, this aspect of the invention extends to the use of a layer containing a nitrite and a layer comprising a source of hydrogen ions in the manufacture of a medicament for the treatment of pain, wherein the layer containing a nitrite and/or the layer comprising a source of hydrogen ions comprises a pharmaceutically active agent and wherein the pharmaceutically active agent is an anaesthetic selected from the group consisting of lignocaine (lidocaine), amethocaine (tetracaine), xylocaine, bupivacaine, prilocaine, ropivacaine, benzocaine, mepivocaine, cocaine or a mixture thereof.

This aspect of the invention also extends to:

A layer containing a nitrite for use in the treatment of a disease or condition, wherein said layer is administered simultaneously, separately or sequentially with a layer comprising a source of hydrogen ions, wherein the layer containing a nitrite and/or the layer comprising a source of hydrogen ions comprises a pharmaceutically active agent.

A layer comprising a source of hydrogen ions for use in the treatment of a disease or condition, wherein said layer is administered simultaneously, separately or sequentially with a layer containing a nitrite, wherein the layer containing a nitrite and/or the layer comprising a source of hydrogen ions comprises a pharmaceutically active agent.

Use of a layer containing a nitrite in the manufacture of a medicament for the treatment of a disease or condition, wherein said layer is administered simultaneously, separately or sequentially with a layer comprising a source of hydrogen ions, wherein the layer containing a nitrite and/or the layer comprising a source of hydrogen ions comprises a pharmaceutically active agent.

Use of a layer comprising a source of hydrogen ions in the manufacture of a medicament for the treatment of a disease or condition, wherein said layer is administered simultaneously, separately or sequentially with a layer containing a nitrite, wherein the layer containing a nitrite and/or the layer comprising a source of hydrogen ions comprises a pharmaceutically active agent.

A system comprising (i) a layer containing a nitrite and (ii) a layer comprising a source of hydrogen ions as a combined preparation for simultaneous, separate or sequential use in treating a disease or condition, wherein the layer containing a nitrite and/or the layer comprising a source of hydrogen ions comprises a pharmaceutically active agent.

In this aspect of the invention, the disease or condition is typically pain and the pharmaceutically active agent is an anaesthetic selected from the group consisting of lignocaine (lidocaine), amethocaine (tetracaine), xylocaine, bupivacaine, prilocaine, ropivacaine, benzocaine, mepivocaine, cocaine or a mixture thereof.

This aspect of the invention also extends to a method of treatment of a disease or condition comprising administering a system of the first aspect of the invention comprising a pharmaceutically active agent to a subject in need thereof. The method typically comprises administering to the patient the first component described herein and then subsequently administering the second component described herein, on top of the first component. The subject is typically a patient suffering from pain. In this embodiment, the pharmaceutically active agent is typically an anaesthetic selected from the group consisting of lignocaine (lidocaine), amethocaine (tetracaine), xylocaine, bupivacaine, prilocaine, ropivacaine, benzocaine, mepivocaine, cocaine or a mixture thereof.

Dosages of the pharmaceutically active agent that is delivered by in this embodiment of the system of the present invention can vary between wide limits, depending upon the disease or disorder to be treated, the severity of the condition, and the age and health of the individual to be treated, etc. and a physician will ultimately determine appropriate dosages to be used. The system is configured so as to deliver the pharmaceutically active agent in a therapeutically active amount, which is an amount that ameliorates or eliminates the symptoms of the disease or disorder that is being treated.

In a sixth aspect, the present invention provides a kit comprising (i) a layer containing a nitrite, and (ii) a layer comprising a source of hydrogen ions as a combined preparation for simultaneous, separate or sequential use in treating a disease or condition wherein the layer containing a nitrite and/or the layer comprising a source of hydrogen ions comprises a pharmaceutically active agent. The disease or condition is typically pain and the pharmaceutically active agent is typically an anaesthetic selected from the group consisting of lignocaine (lidocaine), amethocaine (tetracaine), xylocaine, bupivacaine, prilocaine, ropivacaine, benzocaine, mepivocaine, cocaine or a mixture thereof. The kit is suitably provided with instructions for use in the treatment of the disease or condition.

The present inventors have also previously found that when applied as a pre-treatment, a dressing system of the invention functions to increase the effectiveness of a topically applied aqueous-soluble anaesthetic. The system of the invention can therefore also be used in combination with an aqueous-soluble drug such as an anaesthetic when the dressing system is administered simultaneously with the drug (such as an anaesthetic) or before or after the drug (such as an anaesthetic). In this aspect of the invention, the dressing system of the first aspect of the invention does not include a pharmaceutically active agent; the aqueous-soluble drug is administered separately from the dressing system.

Accordingly, in a seventh aspect, the present invention provides the system of the first aspect of the invention in combination with an aqueous-soluble drug for use in medicine.

By "aqueous-soluble drug" is meant one that for each part of the drug will require 1000 parts or less of an aqueous solvent to solubilise it. In other words, the drug is at least slightly soluble in accordance with the definition given in The United States Pharmacopeia, USP 30-NF 25, 2007 and British Pharmacopoeia, 2009. For example, lidocaine hydrochloride is soluble on this scale requiring 20 parts water to 1 part lidocaine.

Examples of aqueous-soluble drugs for use in accordance with this aspect of the invention include the anti-hypertensive, Atenolol, the water soluble antibiotics, Ampicillin, Streptomycin, Penicillin and the naturally water-soluble vitamins, specifically B and C.

In an eighth aspect, the present invention provides the system of the first aspect of the invention in combination with an anaesthetic for use in the treatment or prevention of pain.

The anaesthetic can be any appropriate anaesthetic for local anaesthesia and is typically selected from the group consisting of lignocaine (lidocaine), amethocaine (tetracaine), xylocaine, bupivacaine, prilocaine, ropivacaine, benzocaine, mepivocaine, cocaine or a mixture thereof. The anaesthetic is typically provided in aqueous or powdered form. For example, anaesthetics such as lidocaine hydrochloride can be provided in the form of a spray of the drug in aqueous form.

The treatment or prevention of pain is typically local anaesthesia but can be the treatment or prevention of any kind of pain. Pain includes chronic and acute pain, post-operative pain and neuropathic pain. Treatment includes both amelioration and prevention (prophylaxis) of pain.

The general concentration range is around 1 to 4%, up to 10% w/w, although greater or lesser amounts can be empirically determined by a physician. Suitably preferred concentrations are tetracaine (0.01 to 10% w/w, suitably 1 to 8% w/w, preferably 2% w/w), lidocaine (0.01 to 10% w/w, suitably 1 to 8% w/w, preferably 5% or 10% w/w) and cocaine (1 to 4% w/w). Generally accepted safe dosages of such compounds for topical anaesthesia in a healthy 70 kg-adult are 750 mg for lidocaine, 200 mg for cocaine, and 50 mg for tetracaine. Other suitable anaesthetics are within the competence of the medical practitioner and can also be used in the system of the present invention at the relevant concentrations.

This aspect of the invention also extends to:

A system of the first aspect of the invention for use in the treatment or prevention of pain, wherein said system is administered simultaneously, separately or sequentially with an anaesthetic.

Use of a system of the first aspect of the invention in the manufacture of a medicament for the treatment or prevention of pain, wherein said system is administered simultaneously, separately or sequentially with an anaesthetic.

This aspect of the invention also extends to a method of treatment or prevention of pain comprising administering a system of the first aspect of the invention and an anaesthetic to a subject in need thereof.

The subject is a patient suffering from pain, or one who is likely to suffer from pain in the future (and therefore is in need of anaesthetic). The method typically comprises either administering to the patient the system of the first aspect of the invention (as a pre-treatment) and then subsequently administering an aqueous-soluble drug such as an anaesthetic, or administering to the patient an aqueous-soluble drug such as an anaesthetic and then subsequently administering the patient the system of the first aspect of the invention. Alternatively, the system of the first aspect of the invention and the aqueous-soluble drug such as an anaesthetic are administered simultaneously.

Preferred features for the second and subsequent aspects of the invention are as for the first aspect mutatis mutandis.

The present invention will now be described by way of illustration only with reference to the following Examples and Figures, in which.

Figure 9:
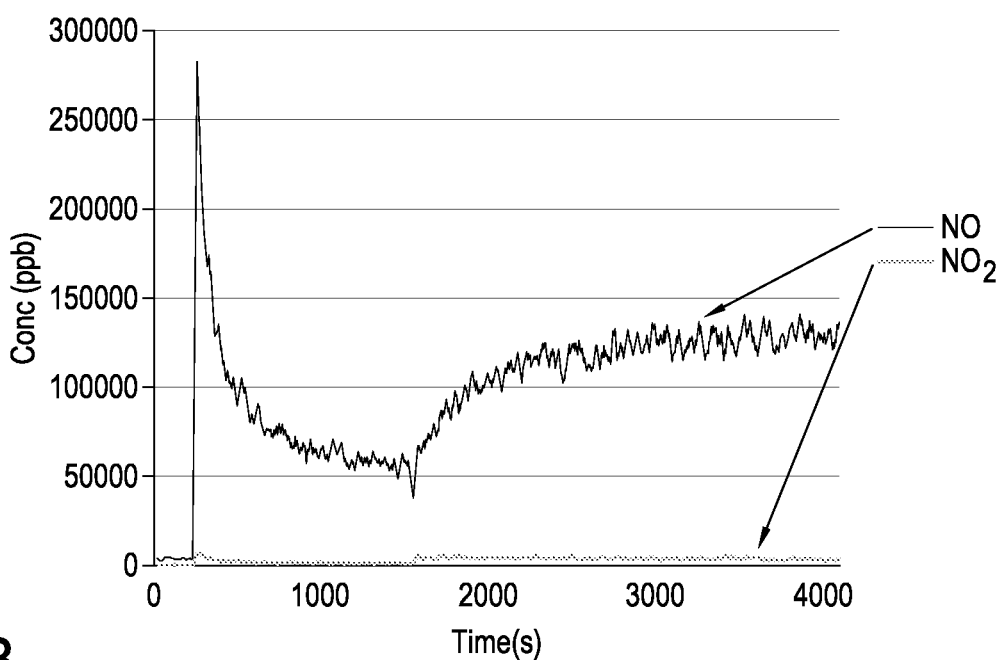
Figure 9:
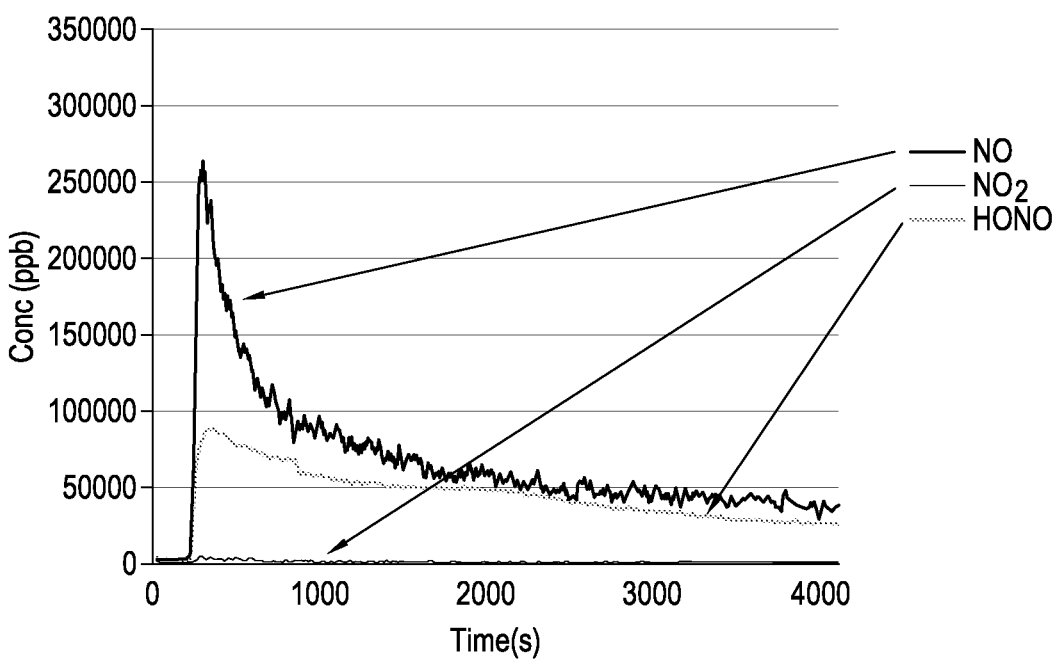

FIG. 9 a plot for a dressing analysis of the full dressing stuck over sampling tube (A) and a plot for a dressing analysis for a quarter dressing face down over sampling tube (B).

Figure 10:
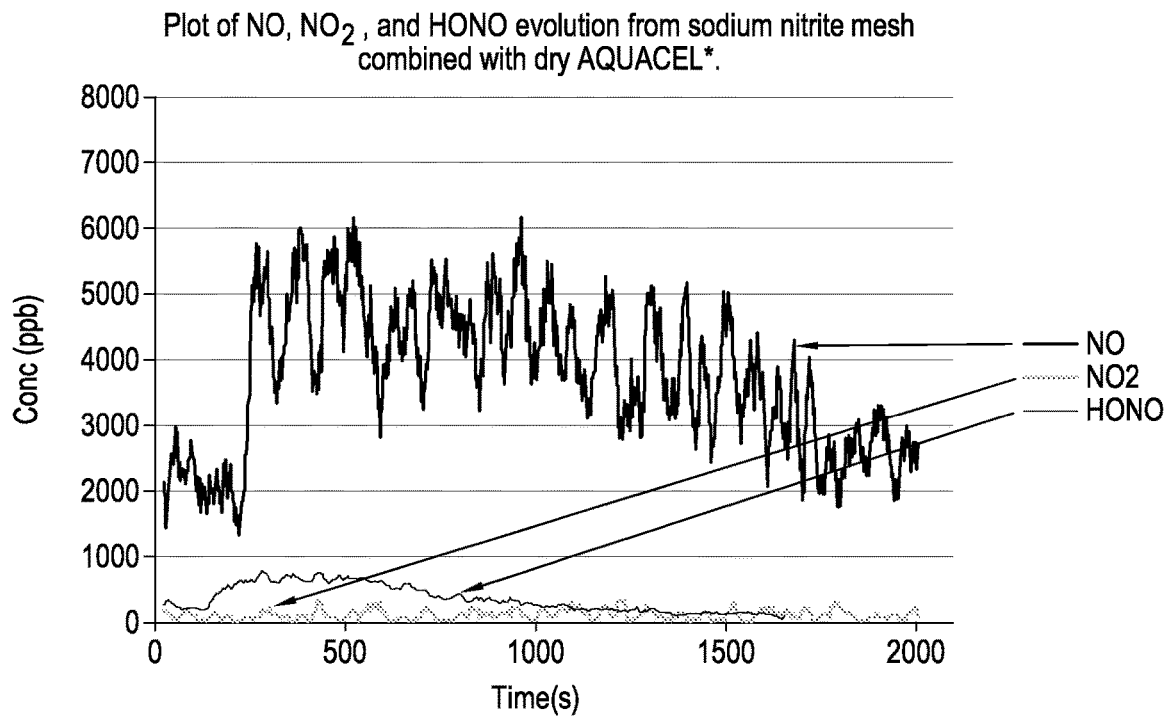

FIG. 10 shows the output from SIFT-MS over time for a nitrite mesh/Aquacel system. As can be seen, the production of NO is favourable compared to $NO_2$ and $HNO_2$ production.

Figure 11:
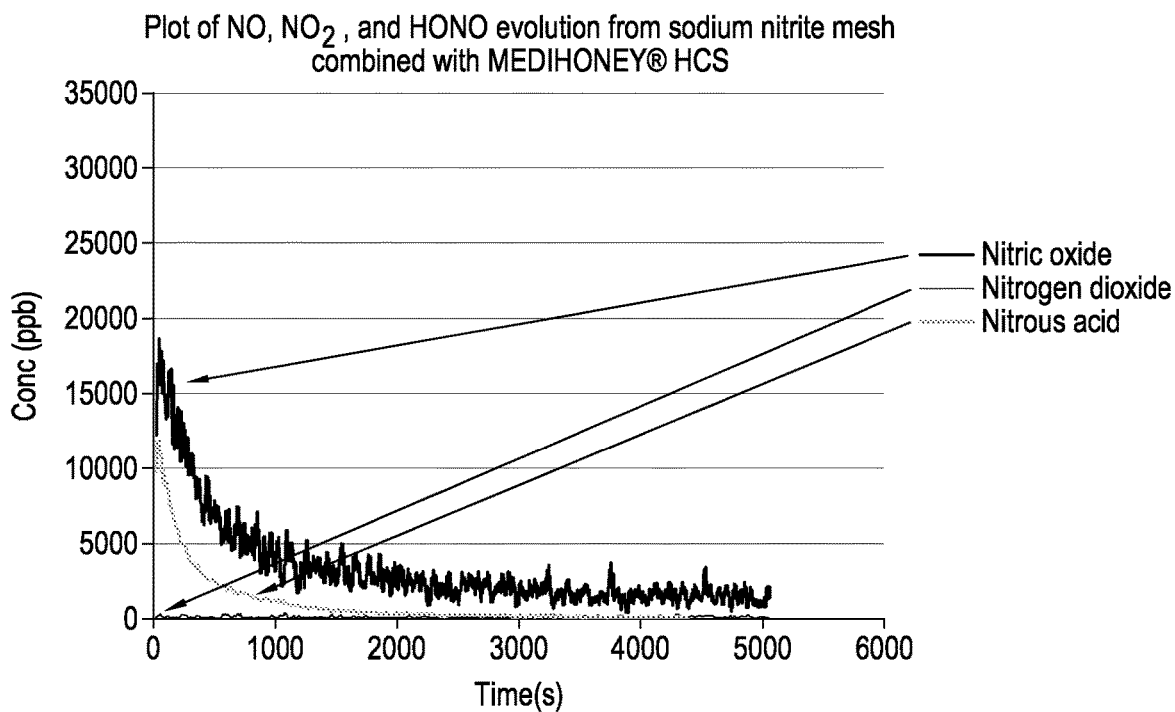

FIG. 11 shows the output from SIFT-MS over time for a nitrite mesh/Medihoney HCS system. As can be seen, the production of NO is favourable compared to $NO_2$ and $HNO_2$ production.

EXAMPLE 1

Selected Ion Flow Tube Mass Spectrometry Analysis of Nitric Oxide Generating Wound Dressing The production of NO, $NO_2$ and $HNO_2$ by a dressing based on a hydrogel system (as described in WO/2014/188174) was tested using Selected Ion Flow Tube Mass Spectrometry (SIFT-MS).

Method

The SIFT-MS system was calibrated for the detection of the compounds of interest using reference samples.

The compounds generated by the dressing system were then tested in a flow cell set up. Briefly, a 670 mL plastic (BPA free) clip lock tub with silicone seal (Tesco) was used and cleaned with low concentration of Virkon detergent before being rinsed with deionised water and dried with paper towel. Two holes were drilled one on either side, one for synthetic air in and one for sample air out. Synthetic air from the cylinder (BOC, the Linde group) (<0.1 parts per million (ppm) NOx) flowed into the chamber whilst a NMP05B micro-pump (KNF Neuberger U.K. Ltd) draws the sample air out of the chamber over the SIFT-MS inlet capillary. The flow rate of air into the chamber was set according to the experiment (either 50 mL/min or 660 mL/min) and sample air was drawn over the capillary at the set flow rate, depending on the experiment (N.B. the SIFT-MS draws air through the capillary at a constant rate of 2.7 mL per minute). In order to achieve higher flow rates two pumps were required. Table 1 shows the various permutations of the undertaken analysis;

| Dressing size | Air Flow | Pump flow | Dressing Position | Analyte | Repeats |
| --- | --- | --- | --- | --- | --- |
| 2.5 × 2.5/5 × 5 | 50 mL/min | 50 mL/min | Face up | $NO/NO_2$ | 2 |
| 2.5 × 2.5/5 × 5 | 50 mL/min | 50 mL/min | Face up | HONO | 2 |
| 2.5 × 2.5/5 × 5 | None | None | Face down | $NO/NO_2$ | 1 |
| 2.5 × 2.5/5 × 5 | None | None | Face down | HONO | 1 |
| Full dressing | 50 mL/min | 50 mL/min | Face up | $NO/NO_2$ | 1 |
| Full dressing | 50 mL/min | 50 mL/min | Face up | HONO | 1 |
| Full dressing | None | None | Face down | $NO/NO_2$ | 1 |
| Full dressing | 50 mL/min | 50 mL/min | Face up | HONO | 1 |
| Full dressing | None | None | Face down | HONO | 1 |
| Full dressing | 660 mL/min | 660 mL/min | Face up | $NO/NO_2$ | 2 |
| Full dressing | 660 mL/min | 660 mL/min | Face up | HONO | 2 |
| 2.5 × 2.5/5 × 5 | 660 mL/min | 660 mL/min | Face up | $NO/NO_2$ | 4 |
| 2.5 × 2.5/5 × 5 | 660 mL/min | 660 mL/min | Face up | HONO | 4 |

Table 1, showing the various permutations of analysis carried out.

All the dressings were treated in the same way; the layers were combined as quickly as possible before the chamber was sealed, though no significant delays were noted it is possible there may have been a few seconds difference between the dressing being combined and the sealing of the chamber. Dressing LOT numbers D020715C/D030515C.

Analysis

The data from the quarter dressing at the 660 mL/min flow rate was converted into excel data. This was used to generate one graph for each dressing showing the production of all three target analytes; and one graph per analyte comparing all four dressings (see results). Duplicate graphs were created with only visible trend lines which have been created using a 25 point moving average in order to smooth out the results by reducing the noise, this step proved useful for performing visual analysis.

Each compound for each dressing was also converted into micrograms (μg) per minute evolved both over the course of the testing duration (1.5 hours) and for the initial 15 minutes (to encompass the initial peak). This was then used to calculate the total quantities in μg for the respective time frames.

Results

The following shows the results for the face up, quarter dressing at the 660 mL/min flow rate method. Four analyses for each analyte were performed using different dressings. Table 2 below shows the quantities calculated for the four different dressings.

TABLE 2 quantification of the compounds evolved from each dressing, each analysis performed with same method. 1 quarter dressing with 660 mL/min flow rate using synthetic air.

|  | Dressing 1 | Dressing 2 | Dressing 3 | Dressing 4 |
|---|---|---|---|---|
| Total AverageHONO (ppm) | 4.23 | 2.47 | 2.18 | 3.18 |
| Average first 15 minutes HONO (ppm) | 17.20 | 9.94 | 8.43 | 12.65 |
| Amount evolved μg/min total HONO | 5.28 | 3.09 | 2.72 | 3.97 |
| Amount evolved μg/min first 15 mins HONO | 21.47 | 12.40 | 10.52 | 15.79 |
| Total HONO evolved μg | 474.89 | 277.94 | 244.42 | 357.44 |
| Total HONO evolved first 15 min (μg) | 322.05 | 186.07 | 157.77 | 236.84 |
| Total Average NO (ppm) | 7.70 | 9.60 | 6.54 | 7.79 |
| Average NO first 15 minutes (ppm) | 28.00 | 37.78 | 25.73 | 28.72 |
| Amount NO evolved μg/min total | 6.12 | 7.62 | 5.19 | 6.18 |
| Amount NO evolved μg/min first 15 mins | 22.23 | 30.00 | 20.43 | 22.80 |
| Total NO evolved μg | 550.44 | 686.05 | 467.04 | 556.34 |
| Total NO evolved first 15 min (μg) | 333.50 | 449.93 | 306.41 | 342.07 |
| Total Average $NO_2$ (ppm) | 0.41 | 0.41 | 0.38 | 0.41 |
| Average $NO_2$ first 15 minutes (ppm) | 0.26 | 0.37 | 0.30 | 0.29 |
| Amount $NO_2$ evolved μg/min total | 0.49 | 0.50 | 0.46 | 0.50 |
| Amount $NO_2$ evolved μg/min first 15 mins | 0.32 | 0.45 | 0.36 | 0.35 |
| Total $NO_2$ evolved μg | 44.55 | 45.01 | 41.48 | 44.88 |
| Total $NO_2$ evolved first 15 min (μg) | 4.74 | 6.71 | 5.42 | 5.28 |

|  | Dressing 1 | Dressing 2 | Dressing 3 | Dressing 4 |
|---|---|---|---|---|
| Total production (μg) | 1069.88 | 1009 | 752.94 | 958.66 |
| Total production first 15 mins (μg) | 660.29 | 642.71 | 469.6 | 584.19 |
| Total dressing production—total empty chamber production (over 90 mins) (μg) | 832.73 | 726.85 | 547.74 | 759.76 |
| Total dressing production—total empty chamber production (first 15 mins) (μg) | 620.77 | 595.68 | 435.4 | 551.04 |

Table 3, the total quantity of measured compounds released over the course of 90 minutes and during the first fifteen minutes, for each dressing. i.e. The value is the result of HONO, NO, $NO_2$ production added together.

|  | Pre-Dressing 1 analysis | Pre-Dressing 2 analysis | Pre-Dressing 3 analysis | Pre-Dressing 4 analysis |
|---|---|---|---|---|
| Total Average HONO (ppm) | 0.21 | 0.32 | 0.15 | 0.14 |
| Amount evolved μg/min total HONO | 0.26 | 0.40 | 0.19 | 0.17 |
| Total HONO evolved μg | 0.53 | 0.80 | 0.39 | 0.34 |
| Total Average NO (ppm) | 2.38 | 2.94 | 1.91 | 1.85 |
| Amount NO evolved μg/min total | 1.89 | 2.34 | 1.52 | 1.47 |
| Total NO evolved μg | 3.81 | 4.71 | 3.07 | 2.97 |
| Total Average $NO_2$ (ppm) | 0.38 | 0.31 | 0.45 | 0.45 |
| Amount $NO_2$ evolved μg/min total | 0.46 | 0.38 | 0.54 | 0.55 |
| Total $NO_2$ evolved μg | 0.93 | 0.76 | 1.10 | 1.11 |
| Total evolved over 120 seconds (μg) | 5.27 | 6.27 | 4.56 | 4.42 |
| Total evolved over 1.5 hours (same as sample time)(μg) | 237.15 | 282.15 | 205.2 | 198.9 |
| Total evolved over first 15 minutes μg | 39.53 | 47.03 | 34.2 | 33.15 |

Table 4, quantity of HONO, NO and $NO_2$ produced by the empty chamber sealed over a 120 second sampling time using synthetic air at a flow rate of 660 mL/min.

|  | Dressing 1 | Dressing 2 | Dressing 3 | Dressing 4 |
|---|---|---|---|---|
| HONO Total average nmol/mL per second | 0.173 | 0.101 | 0.064 | 0.093 |
| HONO total average nmol/mL per min | 10.375 | 6.075 | 3.816 | 5.582 |

|  | Dressing 1 | Dressing 2 | Dressing 3 | Dressing 4 |
|---|---|---|---|---|
| Total amount evolved nmol 90 mins | 933.714 | 546.776 | 343.410 | 502.390 |
| NO total average nmol/mL per second | 0.315 | 0.392 | 0.267 | 0.318 |
| NO total average nmol/mL per min | 18.883 | 23.506 | 16.033 | 19.102 |
| Total amount evolved nmol 90 min | 1699.456 | 2115.520 | 1442.926 | 1719.174 |
| $NO_2$ total average nmol/mL per second | 0.016 | 0.017 | 0.015 | 0.017 |
| $NO_2$ total average nmol/mL per minute | 0.990 | 1.002 | 0.924 | 0.997 |
| $NO_2$ total evolved nmol 90 mins | 89.068 | 90.176 | 83.147 | 89.757 |

Table 5, showing quantification for each compound in nmol.

In order to obtain the μg per minute value the following calculations took place. The molecular weight of the compound at an assumed temperature of 299K was used to calculate the mass per $cm^3$ (1.222 mg for NO). This was then multiplied by the flow rate (average of 650 mL/min) to arrive at 794 mg per minute, for 100% NO i.e. 106 ppm. Thus the equation to convert ppm into mg per minute for NO was therefore $794*(X/10^6)$=mg per minute (where X is the ppm). In order to use uniform significant figures milligrams were converted to micrograms. The same formulae with appropriate coefficients were applied to all three compounds e.g. $1222*(X/10^6)$ for $NO_2$ and $1248*(X/10^6)$ for HONO.

Dressing 3 appears to be an outlier with less production of all three compounds than the other dressings. Excluding dressing 3 the quantities for HONO and NO production shown in table 2 appear to follow an inverse correlation, the dressing with the highest NO value over 1.5 hours also has the lowest HONO value (dressing 2). Likewise the highest HONO producer shows the lowest NO production (dressing 1). This is likely indicative of the conversion of HONO into NO. $NO_2$ appears to have no such relationship with the other compounds produced as the readings were remarkably similar for all 4 dressings.

Table 4 shows the production of HONO, NO and $NO_2$ over 120 seconds with air flow into the sealed chamber before the dressing was added to act as a baseline level. As the sealed chamber with synthetic air flow was not recorded for the same duration as the dressing the average production over the course of 120 seconds was used to calculate the average production over 1.5 hours (the same as testing time). It is worth noting the average production, in ppm is significantly less than seen in table 2. Moreover the total evolved is similar for each test run suggesting there is very limited if any residual detection from the previous sampling. Table 3 shows the total production of the monitored gases over 1.5 hours and the first 15 minutes of a sample run. During the first 15 minutes of sampling there is a spike in production (discussed in detail below). Table 3 also shows the total production of monitored compounds minus the average production from the sealed empty chamber with synthetic air flow at a rate of 660 mL/min (e.g. the same conditions as per sample test).

Figure 1:
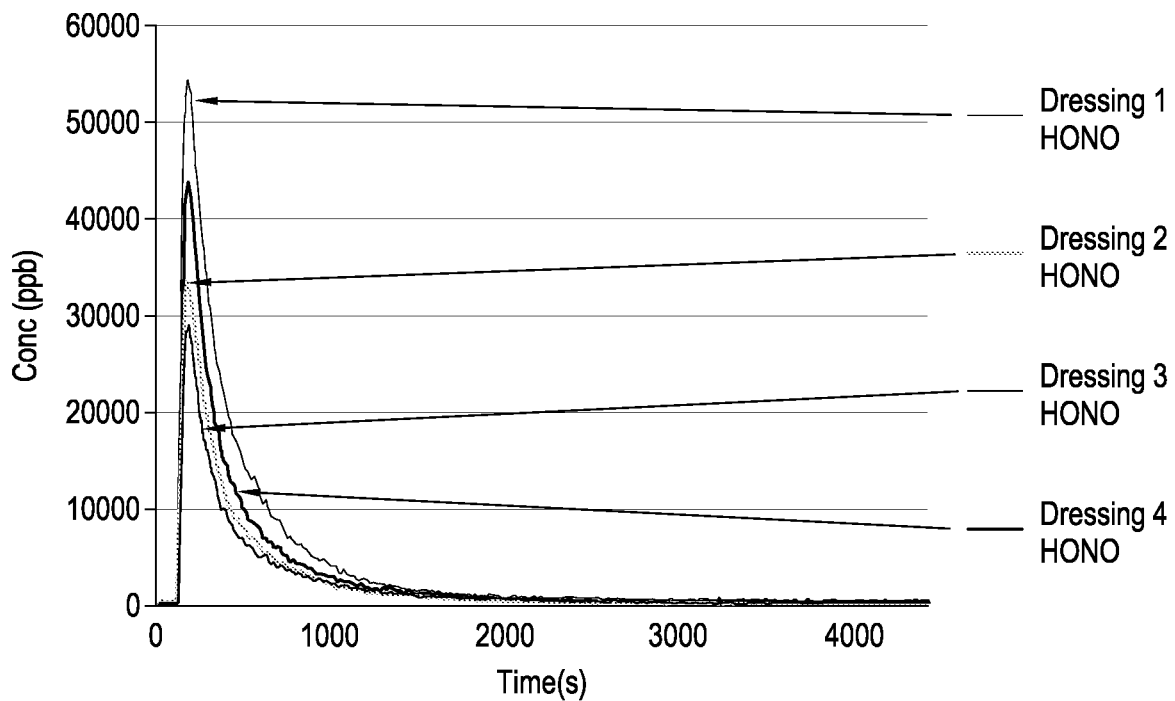
FIG. 1 shows a plot of results for analysis of HONO using 1 quarter dressing (4 repeats) at 660 mL/min flow rate with synthetic air (A); and a plot of results for analysis of HONO using 1 quarter dressing (4 repeats) at 660 mL/min flow rate with synthetic air rescaled for baseline comparison (B).
Figure 1:
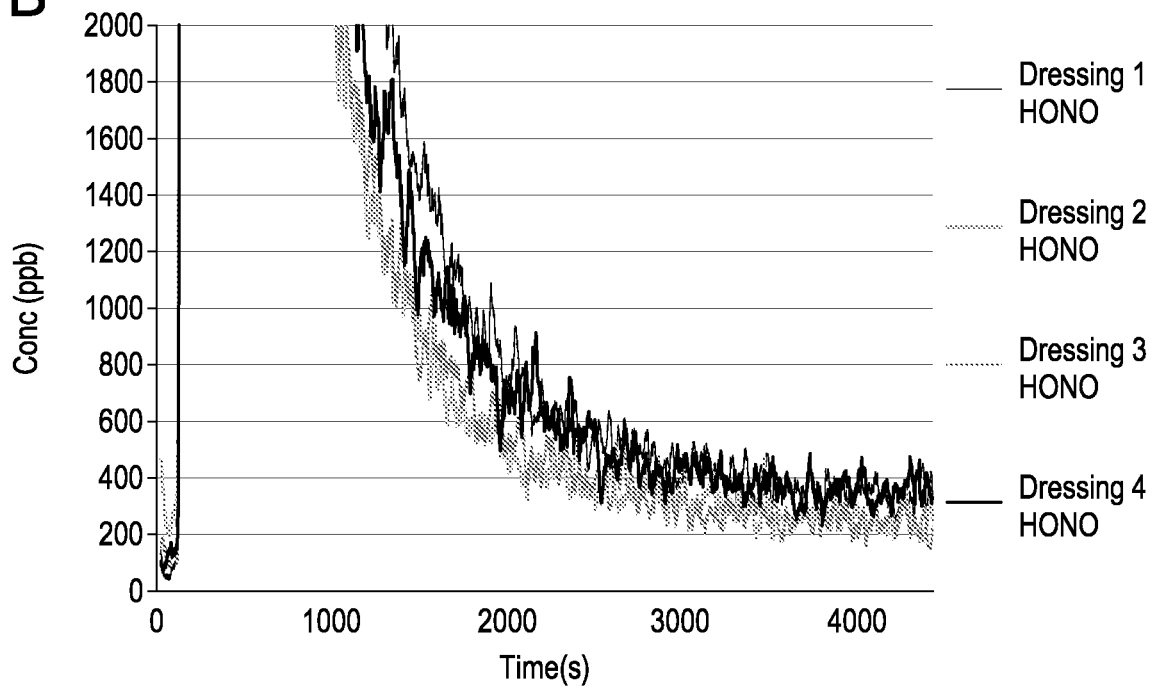
Figure 2:
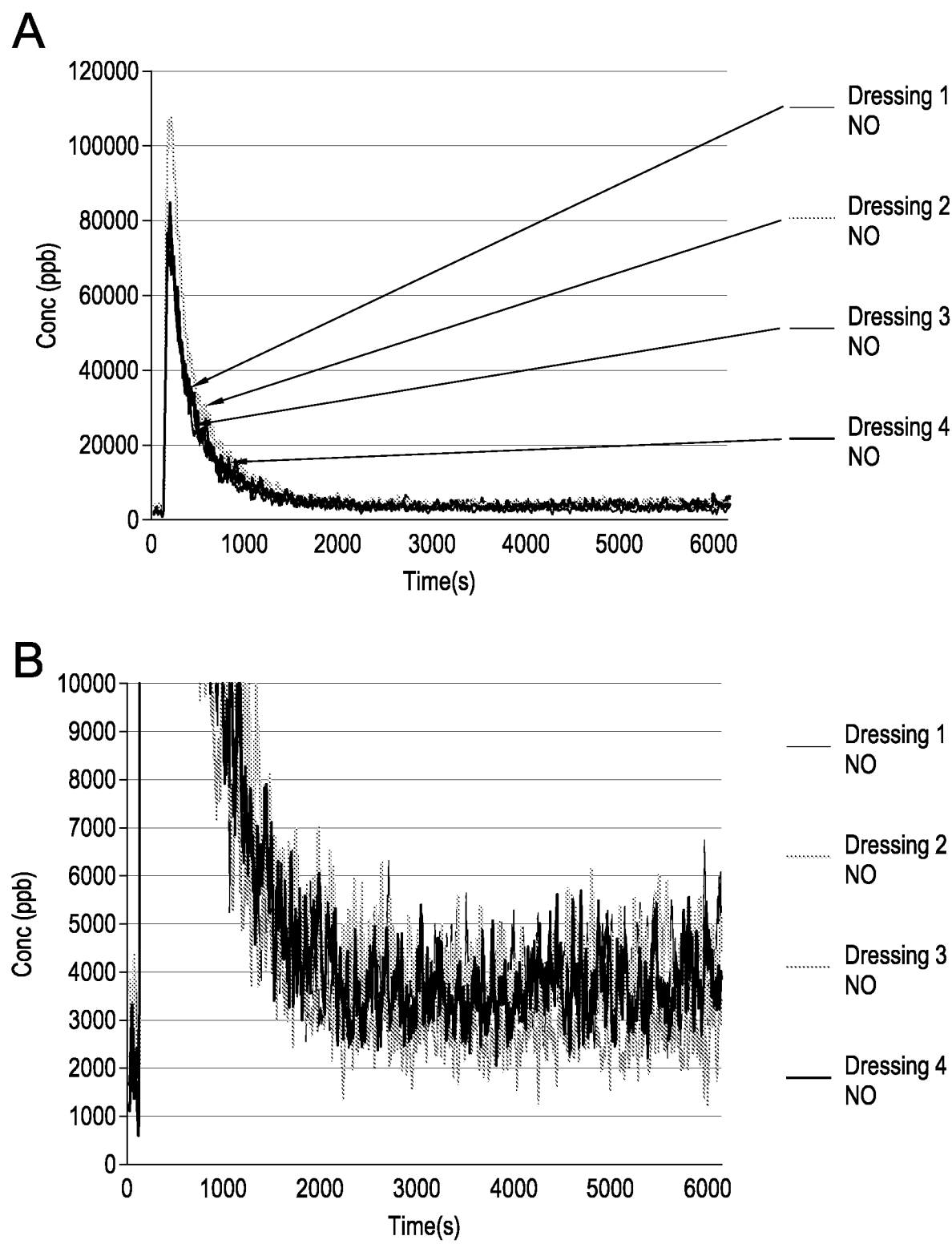
FIG. 2 shows plot of results for analysis of NO using 1 quarter dressing (4 repeats) at 660 mL/min flow rate with synthetic air rescaled (A); and plot of results for analysis of NO using 1 quarter dressing (4 repeats) at 660 mL/min flow rate with synthetic air rescaled for baseline comparison (B).

FIGS. 1 and 2 show the results for all four dressings for HONO and NO production respectively. Both these compounds show similar traits, both show a rapid sharp peak in production almost instantly upon the dressing being assembled and the chamber being sealed. Likewise both compounds appear to drop reasonably rapidly to a steady state of production just above the baseline. The NO production appears to drop to this steady state more rapidly than HONO production; at approximately 1500 seconds and 3000 seconds respectively. There also appears to be a reasonable overlap of the traces at later stages of testing suggesting reasonably consistent production between dressings. However during the initial production spike there are visible differences between the dressings. Furthermore during the first portion of HONO production there is very little noise when compared to NO; however over time the level of noise in HONO production increases.

Figure 3:
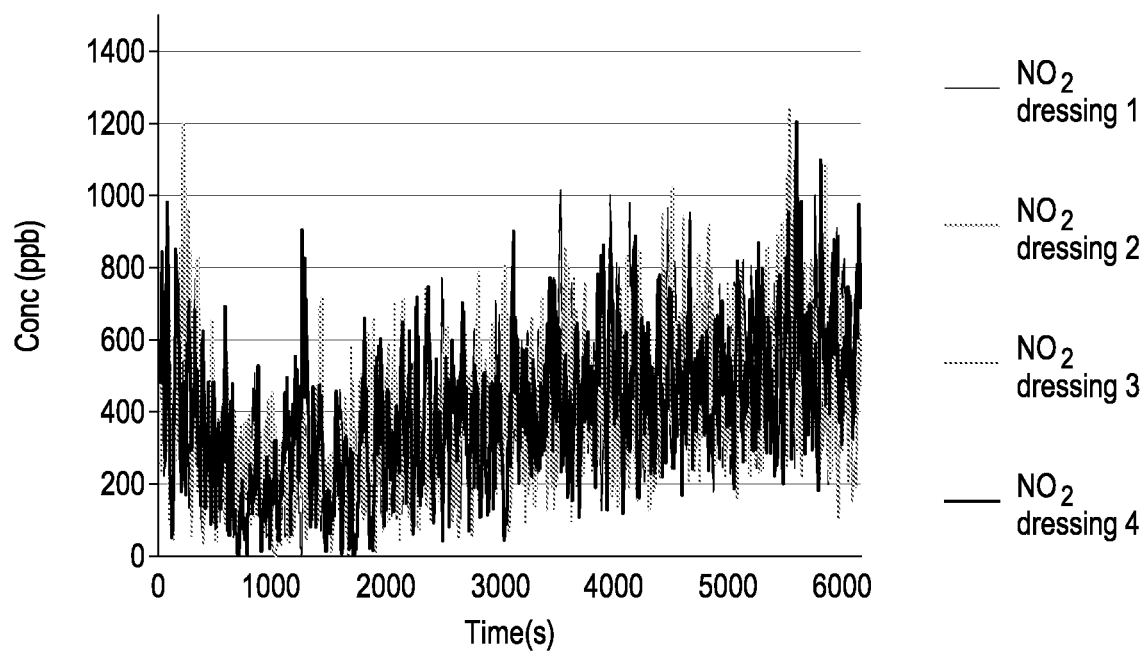
FIG. 3 shows plot of results for $NO_2$ analysis using 1 quarter dressing (4 repeats) at 660 mL/min flow rate using synthetic air.
Figure 4:
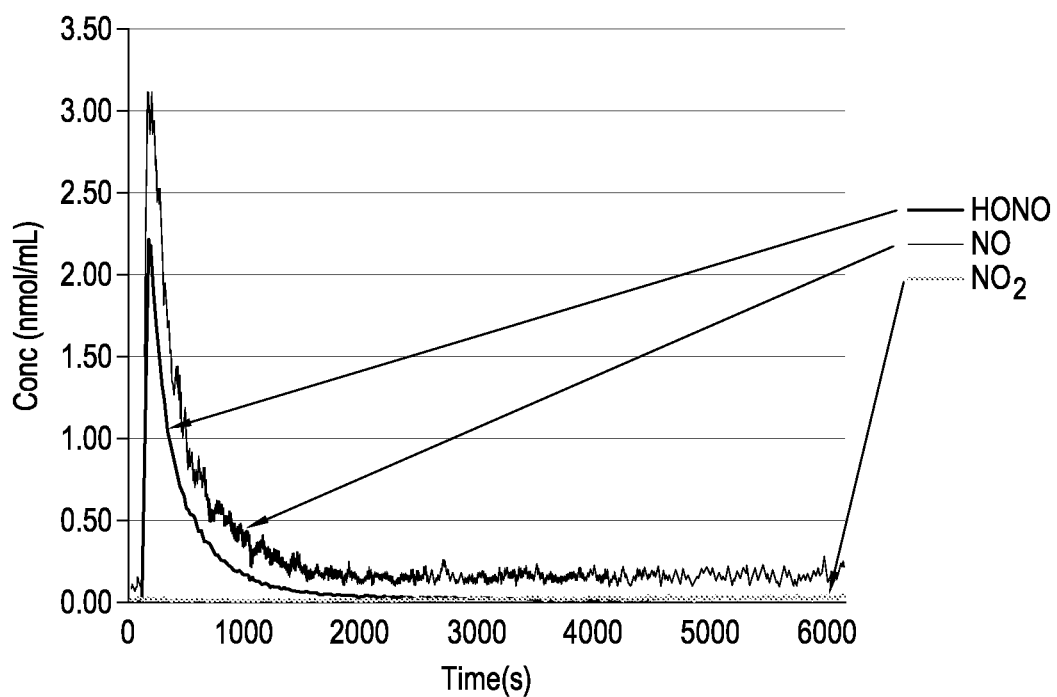
FIG. 4 shows a plot of results for dressing analysis, dressing 1 at 660 mL/min air flow rate, concentration in nmol/mL.
Figure 5:
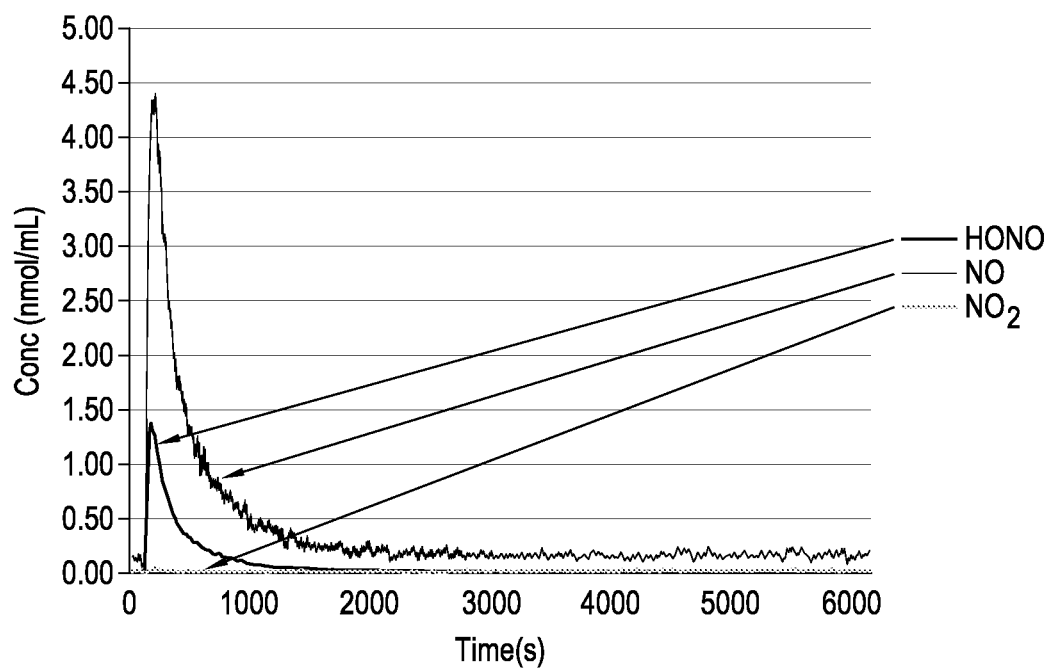
FIG. 5 shows a plot of results for dressing analysis, dressing 2 at 660 mL/min air flow rate, concentration in nmol/mL.
Figure 6:
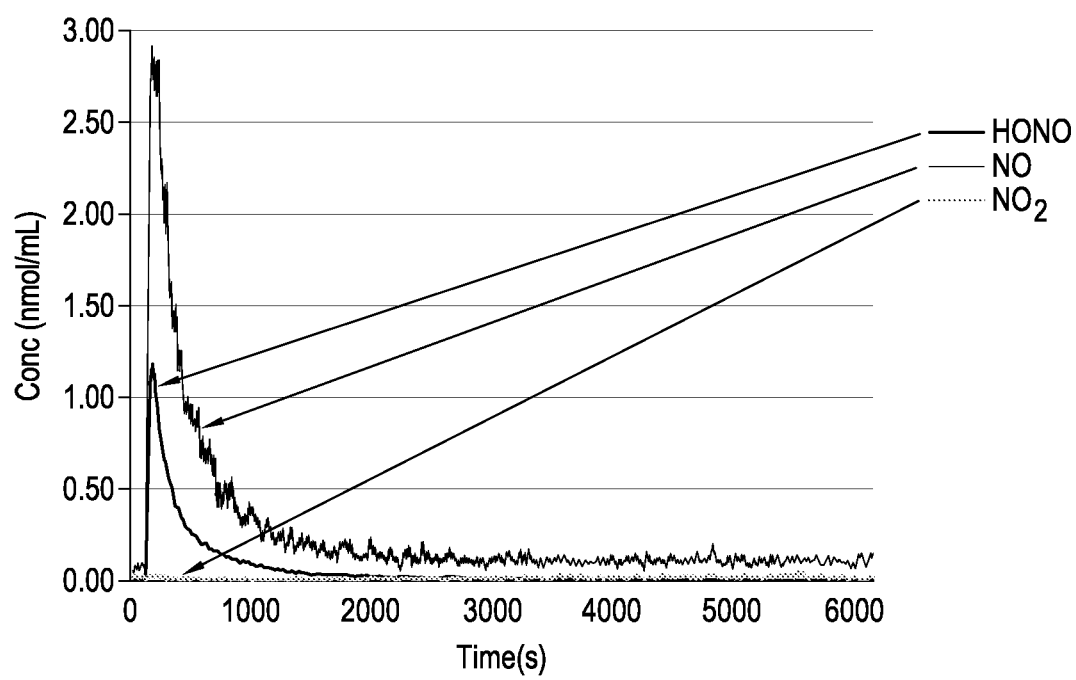
FIG. 6 shows a plot of results for dressing analysis, dressing 3 at 660 mL/min air flow rate, concentration in nmol/mL.
Figure 7:
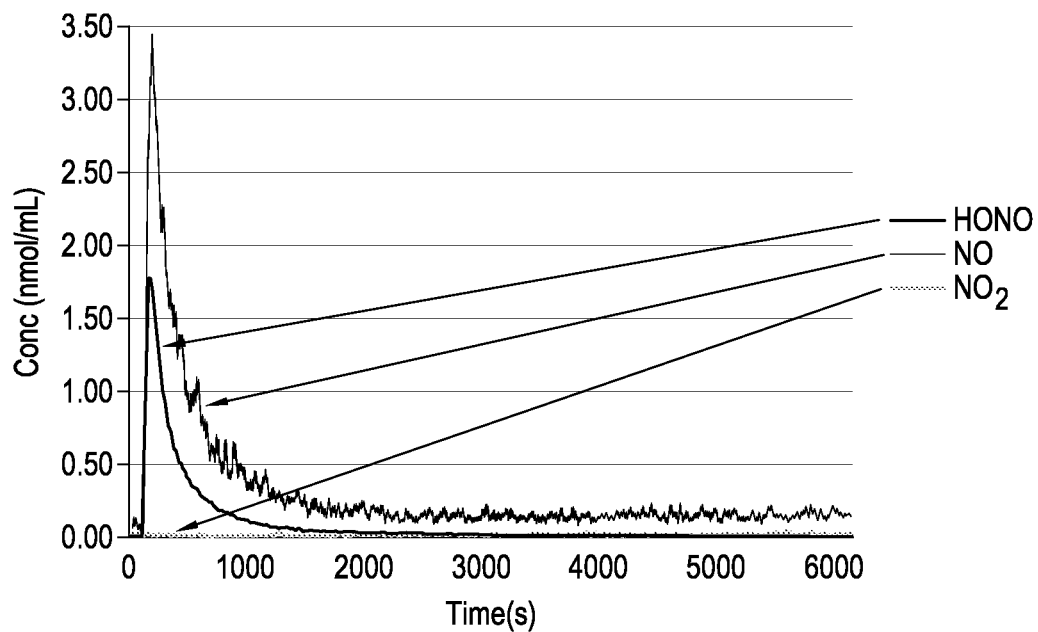
FIG. 7 shows a plot of results for dressing analysis, dressing 4 at 660 mL/min air flow rate, concentration in nmol/mL.

The results for $NO_2$ are shown in FIG. 3, in this instance the pattern of production is unlike the other compounds in that there appears to be a slight dip below the baseline in the initial phase of production. Following this initial phase the levels to rise a steady state; while FIG. 3 may appear very 'noisy' is should be noted the scale is considerably smaller than that of FIGS. 1 and 2. FIGS. 4-7 show the results per dressing allowing a visual representation of how each compound relates to one another, in this context the $NO_2$ production is significantly lower.

FIGS. 4-7 show a plot of NO, HONO and $NO_2$ production at ca. 299K for each dressing converted into nmol/mL. This was calculated using the equation X ppm=$0.0408*X$ nmol/mL. Total quantification for each compound (in nmol) is shown in table 5. As noted earlier all dressings show consistent patterns in the production of all three compounds of interest. It is worth noting that across the whole testing time frame the production of NO appears to be significantly greater than that of the other compounds. This is highlighted by the yield calculations of table 2. It is known that at the lower levels of detection (e.g. sub parts per million) NO detection becomes difficult on SIFT-MS due to interference from the NO+ reagent ion. This is mitigated by the proportionally large production of NO from the dressing.

Figure 8:
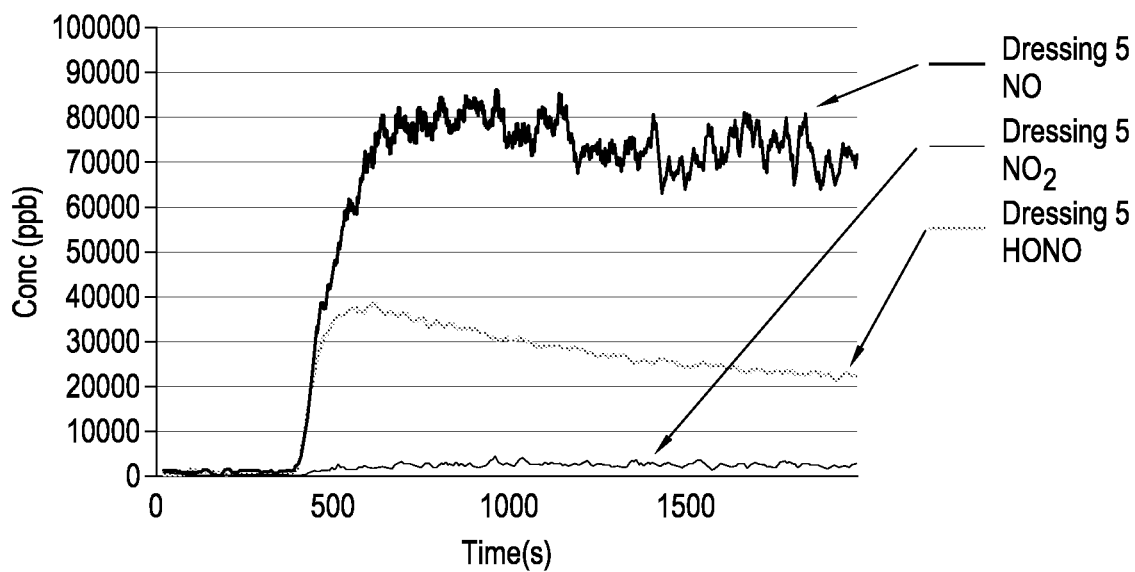
FIG. 8 shows a plot for a dressing analysis, quarter dressing at the 50 mL/min synthetic air flow rate.

As mentioned all four repeats discussed thus far have been with airflow over the dressing of 660 mL/min. In the initial phase of testing a run was done with a significantly lower flow of the same synthetic air at approximately 50 mL/min (FIG. 8). At the lower flow the patterns in production are broadly similar to that of the higher flow rate in so far as there is an almost instant spike upon sealing the chamber followed by a drop in production to a steady state (with the exception of $NO_2$). However in this instance the steady state of production occurs at a significantly higher level than at the higher flow rate. This is most likely attributed to the possibility that production occurs at a more rapid rate than the air can leave the chamber and thus the gases are collected and in effect concentrated. Alternatively the higher flow rate may be providing a dilution effect which would also result in this pattern. Following this method of testing the chamber takes significantly longer to return to an appropriate baseline level than after higher flow rate testing. This therefore provides us with evidence that for this particular permutation of testing the higher 660 mL/min flow rate is more appropriate.

In order to achieve something of an analogue to an in vivo test the dressing was also analysed face down stuck over the sample inlet tube; the gathered results can be seen in FIG. 9. For this experiment no air flow was used and the chamber lid was removed, thus eliminating any concentration effects from the chamber. The HONO trace is not included for the full dressing analysis as this was part of another trace and would make for an inappropriate comparison. Once again we see a familiar pattern in the production of each compound. The NO peak while monitoring facedown is very sharp, it is also notable that the difference between the peak production for the full and quarter dressing is not as large as anticipated; approximately 280 to 260 ppm respectively. The full dressings steady state is significantly higher (125 ppm full dressing 40 ppm quarter dressing), though this this is not as big as expected. If a quarter dressing on average produces 40 ppm one might expect the whole dressing to produce 160 ppm (4 times the amount), we find this does not occur and thus hypothesis that there may be a relationship between the edges surface area and NO production. HONO production during the steady state for the full dressing was approximately 100 ppm compared to approximately 25 ppm for the quarter dressing; these proportions are what one would expect from a linear relationship between surface area and HONO production.

Conclusion

The nitric oxide producing dressing has been analysed for production of NO, $NO_2$ and HONO under a number of different permutations. The proportions of the compounds produced remained very similar: $NO_2$ production is by far the least abundant regardless of methodology. HONO is produced in significant quantities and appears to have an inverse relationship with NO; thus it is important when considering the chemical processes taking place. As expected NO production is by far the most consistent and abundant compound (of those monitored).

The finding that high levels of NO and very low levels of $NO_2$ are produced is surprising, since until now it was assumed that acidification of nitrite would give rise to equimolar ratios of NO and $NO_2$.

EXAMPLE 2

Production of Dressing System Using Hydrogel Compositions

Primary Layer: Wound Contact Mesh (containing 1M Sodium Nitrite)

The Mesh is a polypropylene mesh (RKW-Group), imbibed with 1M Sodium Nitrite solution, from Sodium Nitrite Extra Pure ph Eur, USP Merck and deionised water.

Description of Manufacturing Process

Sodium nitrite is weighed into a suitably sized vessel and then transferred carefully into a known volume of deionised water, which is then stirred until dissolution is complete to make a solution of appropriate concentration. In this embodiment the sodium nitrite solution is dispensed onto the mesh and then is placed into each petri dish for a minimum time to imbibe the mesh with the sodium nitrite solution. The finished products are sterilised by irradiation.

Secondary Layer: Hydrogel Top Layer

The hydrogel chosen for this study has high capability for absorption and facilitates a moist wound-healing environment. The hydrogel comprises a cross-linked anionic copolymer, circa 30% water and circa 30% glycerol. It has an outer polyurethane film that provides a bacterial barrier and aesthetically pleasing outer surface to the dressing. The gels have an acidic surface pH circa 2-5 arising from the presence of some sulfonic acid groups. These groups provide the acidity for the conversion of Sodium Nitrite to Nitric Oxide. As the sulfonic acid groups are covalently bound to the hydrogel network they are not released into the wound.

Description of Manufacturing Process

The hydrogel is manufactured from the list of ingredients set out below. The process of manufacture is as according to patents EP1100555B1 and EP110556B1, which are incorporated by reference in their entirety herein.

The ingredients are dispensed into a suitable mixing vessel (dispensing is controlled by weight) and stirred overnight. Once mixed, a portion of the liquid solution is dispensed onto a moving substrate (clear polyurethane film, Inspire 2304) at the required coat weight. Then a mesh made of polypropylene (RKW 20 $g/m^2$) is laid onto the top of the liquid formulation, which is then exposed to UV light and cured. A second layer is coated on top of the first at the required coat weight and exposed to UV light, thus making a "sandwich" with the mesh in the middle.

The hydrogel is cut to the required size and pouched, sealed and sterilised. The finished products are sterilised by gamma irradiation.

The components of the hydrogels are:
Monomer, Sodium AMPS 2405A (58% solution in water) (Lubrizol)
Monomer, 2-acrylamido-2-methylpropane sulfonic acid (Sigma-Aldrich)(AMPS Acid)
Monomer, Acrylic Acid (BASF)
Glycerine BP, EP (H. Fosters)
Darocur 1173, 2-hydroxy-2-methylpropiophenone (BASF) (D1173)
SR 344, poly (ethylene glycol) diacrylate (Sartomer) (PEG diacylate)
Mesh, Carded non-woven 20 gsm (RKW-Group)
Inspire 2304, polyurethane film (Coveris)
70 micron, low density polyethylene, siliconised (Adcoat)
'NeoCarta,' peelable laminate (Safta)
The components of the nitrite layer are:
Mesh, Carded non-woven 20 gsm (RKW-Group)
'NeoCarta,' peelable laminate (Safta)
Sodium Nitrite, extra pure, Ph Eur, USP (Merck)
De-ionised water (First Water Ltd)
Example Hydrogel Compositions

| Component | Sample 1 Parts (g) | Sample 2 Parts (g) | Sample 3 Parts | Sample 4 Parts (g) |
|---|---|---|---|---|
| Na AMPS 2405A | 66 | 67 | 67 | 67 |
| AMPS Acid | 1.03 | 0.4 | 0.05 | — |
| Acrylic Acid | — | — | — | 2 |
| Glycerol | 30 | 30 | 30 | 30 |
| D1173 and PEG diacrylate (in a 4:20 w/w ratio) | 0.12 | 0.12 | 0.12 | 0.12 |

Table 6, example hydrogel compositions.

EXAMPLE 3

Production of a Wound Dressing

A wound dressing of the invention can be made by placing the first layer, made by imbibing a 5 cm×5 cm "nitrite mesh" of Example 2 with 0.05 to 1 g of 0.01M to 2M sodium nitrite, (specific example 0.2 g of 1M sodium nitrite) onto a wound and covering the first layer with a second layer comprising a source of hydrogen ions. The second layer may be for example Medihoney HCS (11 cm×11 cm) (Derma Sciences),
AQUACEL® (10 cm×10 cm) (ConvaTec), AQUACEL® Ag (10 cm×10 cm) (ConvaTec), AQUACEL® Ag Foam (10 cm×10 cm (ConvaTec)), AQUACEL® Foam (10 cm×10 cm) (ConvaTec), AQUACEL® EXTRA (10 cm×10 cm) (ConvaTec), Granuflex (10 cm×10 cm) (ConvaTec).

EXAMPLE 4

Selected Ion Flow Tube Mass Spectrometry Analysis of Alternative Nitric Oxide Generating Dressing Systems The production of NO, $NO_2$ and $HNO_2$ by dressings based on either Medihoney or AQUACEL was tested using Selected Ion Flow Tube Mass Spectrometry (SIFT-MS).

SIFT-MS was carried out as described with respect to Example 1, using a flow rate of 660 ml/min.

AQUACEL is carboxymethyl cellulose based fibre, in which carboxylic acid groups are copolymerised into the polymer network. In this experiment, a dry AQUACEL (10 cm×10 cm) (ConVatec) dressing was cut in half to form a 5 cm×5 cm square and placed into the sample chamber. A 2.5 cm×2.5 cm (0.0145 mg) of polypropylene non-woven mesh imbibed with 34.5 mg of a 1M sodium nitrite solution was placed on top of the Aquacel sample and the sample chamber then closed and SIFT-MS data collected. FIG. 10 shows the output from SIFT-MS for this experiment. As can be seen, the production of NO is favourable compared to $NO_2$ and $HNO_2$ production.

Medihoney HCS is a gel dressing comprising greater than 50% Manuka honey. In the following experiment Medihoney HCS was used as the sole source of hydrogen ions. A Medihoney HCS (10 cm×10 cm) (Derma Sciences) dressing was cut in half to form a 5 cm×5 cm square and placed into the sample chamber. A 2.5 cm×2.5 cm (0.0145 mg) of polypropylene non-woven mesh imbibed with 34.5 mg of a 1M sodium nitrite solution was placed on top of the Medihoney sample and the sample chamber then closed and SIFT-MS data collected. FIG. 11 shows the output from SIFT-MS for this experiment. As can be seen, the production of NO is favourable compared to $NO_2$ and $HNO_2$ production.

The invention claimed is:

1. A system comprising:
   (i) a layer containing a nitrite, wherein the layer containing the nitrite is a mesh or a dissolvable film; and
   (ii) a layer comprising a source of hydrogen ions, wherein the layer is not a hydrogel.

2. The system according to claim 1, wherein the layer containing the nitrite is a mesh.

3. The system according to claim 2, wherein the mesh is formed of a polymer.

4. The system according to claim 1, wherein the layer containing the nitrite is a dissolvable film.

5. The system according to claim 4, wherein the dissolvable film is formed of a polyvinyl alcohol, polyvinylpyrrolidone, a cellulose-based polymer or cellulose.

6. The system according to claim 1, wherein the nitrite is an alkaline metal nitrite or an alkaline earth metal nitrite.

7. The system according to claim 6, wherein the nitrite is sodium nitrite.

8. The system according to claim 1, wherein the system comprises a plurality of layers containing a nitrite.

9. The system according to claim 1, wherein the nitrite is present as a nitrite solution.

10. The system according to claim 1, wherein the layer comprising the source of hydrogen ions is a superabsorbent dressing based on sodium polyacrylate.

11. The system according to claim 1, wherein the layer comprising the source of hydrogen ions is a honey-based dressing.

12. A method for the treatment of a condition associated with tissue ischaemia or a wound, comprising administering the system according to claim 1 to a subject in need thereof.

13. The method according to claim 12, wherein the wound is an ulcer.

14. The method according to claim 13, wherein the ulcer is a leg ulcer, pressure ulcer, or diabetic ulcer.

15. The method according to claim 12, wherein the wound is a skin donor site, a surgical wound, a burn, a laceration, or an abrasion.

16. The method according to claim 12, wherein the condition associated with tissue ischaemia is Raynaud's syndrome, or tissue ischaemia caused by septic shock, irradiation, or a peripheral vascular disease.

17. The system according to claim 1, further comprising a pharmaceutically active agent.

18. A method for the treatment of a disease or medical condition, comprising administering the system according to claim 17 to a subject in need thereof.

19. A kit comprising:
   (i) a layer containing a nitrite, wherein the layer containing the nitrite is a mesh or a dissolvable film, and
   (ii) a layer comprising a source of hydrogen ions, wherein the layer is not a hydrogel, as a combined preparation for simultaneous, separate or sequential use in treating a disease or condition, wherein the layer containing the nitrite and/or the layer comprising the source of hydrogen ions comprises a pharmaceutically active agent.

20. A system comprising:
   (i) a layer containing a nitrite, wherein the layer containing the nitrite is a mesh or a dissolvable film; and
   (ii) a layer comprising a source of hydrogen ions, wherein the layer is not a hydrogel, in combination with an anaesthetic.

21. A method of treatment or prevention of pain comprising administering a system comprising:
   (i) a layer containing a nitrite, wherein the layer containing the nitrite is a mesh or a dissolvable film; and
   (ii) a layer comprising a source of hydrogen ions, wherein the layer is not a hydrogel, and an anaesthetic to a subject in need thereof.

* * * * *